US005783693A

United States Patent [19]
Bertozzi et al.

[11] Patent Number: 5,783,693
[45] Date of Patent: Jul. 21, 1998

[54] METHODS FOR SYNTHESIZING SULFATED DISACCHARIDE INHIBITORS OF SELECTINS

[75] Inventors: Carolyn Bertozzi; Steven D. Rosen, both of San Francisco, Calif.

[73] Assignee: The Regents of the University of California, Oakland, Calif.

[21] Appl. No.: 518,381

[22] Filed: Aug. 23, 1995

Related U.S. Application Data

[63] Continuation-in-part of Ser. No. 432,849, May 2, 1995, Pat. No. 5,489,578, which is a continuation of Ser. No. 155,947, Nov. 10, 1993, abandoned.

[51] Int. Cl.$^6$ .............................. C07H 1/00; C07H 15/00
[52] U.S. Cl. .................. 536/124; 536/4.1; 536/18.5; 536/123.13; 514/25; 514/53; 514/61
[58] Field of Search ............................... 536/4.1, 18.5, 536/123.13, 124; 514/25, 53, 61

[56] References Cited

U.S. PATENT DOCUMENTS

| 5,211,937 | 5/1993 | Brandley et al. | 424/1.1 |
|---|---|---|---|
| 5,428,025 | 6/1995 | Brandley et al. | 514/55 |

FOREIGN PATENT DOCUMENTS

| WO 91/19502 | 12/1991 | WIPO. |
|---|---|---|
| 93/00908 | 1/1993 | WIPO. |
| WO 93/00908 | 1/1993 | WIPO. |
| 94/00477 | 1/1994 | WIPO. |
| WO 94/00477 | 1/1994 | WIPO. |

OTHER PUBLICATIONS

Baumheuter, S., et al., (1993) "Binding of L-selectin to the Vascular Sialomucin CD43," *Science* 262:436–438.
Berg, E.L., et al., (1989) "Homing Receptors and Vascular Addressins: Cell Adhesion Molecules That Direct Lymphocyte Traffic," *Immunol. Rev.* 108:5–18.
Brandley, B.K., et al., (1993) "Structure–function Studies on Selectin Carbohydrate Ligands. Modifications to Fucose, Sialic Acid and Sulphate as a Sialic Acid Replacement," *Glycobiology* 3:633–639.
Briskin, M.J., et al., (1993) "MAdCAM-1 Homology to Immunoglobulin and Mucin–like Adhesion Receptors and to IgA1," *Nature* 363:461–464.
Buerke, M., et al., (1994) "Sialyl Lewis$^x$-containing Oligosaccharide Attenuates Myocardial Reperfusion Injury in Cats," *J. Clin. Invest.* 93:1140–1148.
Capon, C., et al., (1989) "Structures of O–glycosidically Linked Oligosaccharides Isolated from Human Meconium Glycoproteins," *Eur. J. Biochem.* 182: 139–52.
Duijvestijn, A., and Hamann, A., (1989) "Mechanisms and Regulation of Lymphocyte Migration," *Immunol. Today* 10:23–28.
Dumas, D.P., et al. (1991) "Enzymatic Synthesis of Sialyl Le$^x$ and Derivatives Based on a Recombinant Fucosyltransferase," *Bioorg. Med. Chem. Lett.* 1:425–428.

Gallatin, M.W., et al., (1983) "A Cell–surface Molecule Involved in Organ–specific Homing of Lymphocytes," *Nature* 304:30–34.
Gallatin, M.W., et al., (1986) "Lymphocyte Homing Receptors," *Cell* 44:673–680.
Green, P.J., et al., (1992) "High Affinity Binding of the Leukocyte Adhesion Molecule L–selectin to 3'–sulphated–Le$^a$ and –Le$^x$ Oligosaccharides and the Predominance of Sulphate in This Interaction Demonstrated by Binding Studies With a Series of Lipid–linked Oligosaccharides," *Biochem. Biophys. Res. Commun.* 188(1):244–251.
Hemmerich, S., et al., (1995) "Structure of the o–Glycans in GlyCAM-1, and Endothelial–derived Ligand for L–selectin," *J. Biol. Chem.* 270:12035–12047.
Imai, Y., et al., (1992) "Further Characterization of the Interaction Between L–selectin and Its Endothelial Ligands," *Glycobiology* 2:373–381.
Imai, Y., et al., (1993) "Sulphation Requirement for ICAM–1, and Endothelial Ligand for L–selectin," *Nature* 361:555–557.
Jacob, G.S., et al., (1995) "Binding of Sialyl Lewis X to E–selectin as Measured by Fluorescence Polarization," *Biochemistry* 34:1210–1217.
Langer, R., (1990) "New Methods of Drug Delivery," *Science* 249:1527–1533.
Lasky, L.A., et al., (1992) "An Endothelial Ligand for L–selectin Is a Novel Mucin–like Molecule," *Cell* 69:927–938.
Lewinsohn, D.M., et al., (1987) "Leukocyte–Endothelial Cell Recognition: Evidence of a Common Molecular Mechanism Shared by Neutrophils, Lymphocytes, and Other Leukocytes," *J. Immunol.* 138:4313–4321.
Ma, X., et al., (1993) "Monoclonal Antibody to L–selectin Attenuates Neutrophil Accumulation and Protects Ischemic Reperfused Cat Myocardium," *Circulation* 88:649–658.
Mawhinney, T.P., et al., (1992) "Sulfated Sialyl–oligosaccharides Derived from Tracheobronchial Mucous Glycoproteins of a Patient Suffering from Cystic Fibrosis," *Carbohydrate Res.* 235:179–197.
Mihelcic, D., et al., (1994) "Inhibition of Leukocyte L–selectin Function With a Monoclonal Antibody Attenuates Reperfusion Injury to the Rabbit Ear," *Blood* 84:2322–2328.
Mulligan, M.S., et al., (1993) "Protective Effects of Sialylated Oligosaccharides in Immune Complex–induced Acute Lung Injury," *J. Exp. Med.* 178:623–631.
Mulligan, M.S., et al., (1993) "Protective Effects of Oligosaccharides in P–selectin–dependent Lung Injury," *Nature* 364:149–151.

(List continued on next page.)

*Primary Examiner*—Kathleen K. Fonda
*Attorney, Agent, or Firm*—Karl Bozicevic; Bozicevic & Reed LLP; Bret E. Field

[57] ABSTRACT

Sulfated disaccharides characterized by the ability to inhibit the binding of selectin to its physiologically-relevant ligand are disclosed. Included are efficient and inexpensive methods for producing the sulfated disaccharides, and methods for their therapeutic use and in in vivo and in vitro assays.

6 Claims, 4 Drawing Sheets

OTHER PUBLICATIONS

Mulligan, M.S., et al., (1994) "Requirements for L–Selectin in Neutrophil–Mediated Lung Injury in Rats," *J. Immunol.* 152:832–840.

Needham, L.K., et al., (1993) "The HNK–1 Reactive Sulfoglucuronyl Glycolipids for L–selectin and P–selectin But Not E–selectin," *Proc. Natl. Acad. Sci. USA* 90:1359–1363.

Nicolaou, K.C., et al., (1991) "Sterocontrolled Synthesis of Sialyl Le$^x$, the Oligosaccharide Binding Ligand to ELAM–1 (Sialyl=N–acetylneuramin)," *J. Chem. Soc., Chem. Commun.* pp. 870–872.

Nicolaou, K.C., et al., (1992) "Total Synthesis of Sialyl Dimeric Le$^x$," *J. Am. Chem Soc.* 114:3126–3128.

Palcic, M.M., (1994) "Glycosyltransferases in Glycobiology," *Meth. Enzymol.* 230:300–316.

Rao, B.N.N., et al. (1994) "Sialyl Lewis X Mimics Derived from a Pharmacophore Search Are Selectin Inhibitors With Anti–inflammatory Activity," *J. Biol. Chem.* 269:19663–19666.

Rosen, S.D., (1989) "Lymphocyte Homing: Progress and Prospects," *Curr. Opin. Cell. Biol.* 1:913–919.

Rosen, S.D., and Bertozzi, C.R., (1994) "The Selectins and Their Ligands," *Curr. Op. Cell Biol.* 6:663–673.

Scudder, P.R., et al., (1994) "Enzymatic Synthesis of a 6'–sulphated Sialyl–Lewis$^x$ Which Is an Inhibitor of L–Selectin Binding to Peripheral Addressin," *Glycobiology* 4:929–933.

Seekamp, A., et al., (1994) "Role of Selectins in Local and Remote Tissue Injury Following Ischemia and Reperfusion," *Am. J. Pathol.* 144:592–598.

Springer, T.A., (1990) "Adhesion Receptors of the Immune System," *Nature* 346:425–434.

Stahl, W., et al., (1994) "Synthesis of Deoxy Sialyl Lewis$^x$ Analogues, Potential Selectin Antagonists," *Angew. Chem. Int. Ed. Engl.* 33:2096–2098.

Stoolman, L.M., (1989) "Adhesion Molecules Controlling Lymphocyte Migration," *Cell* 56:907–910.

Suzuki, Y., et al., 1993, "Sulfated Glycolipids Are Ligands for a Lymphocyte Homing Receptor, L–selectin (LECAM–1), Binding Epitope in Sulfated Sugar Chain," *Biochem. Biophys. Res. Commun.* 190(2): 426–434.

Uchiyama, T., et al., (1995) "Design and Synthesis of Sialyl Lewis X Mimetics," *J. Am Chem. Soc.* 117:5395–5396.

Varki, A., (1994) "Selectin Ligands," *Proc. Natl. Acad. Sci. USA* 91:7390–7397.

Watson, S.R., et al., (1990) "A Homing Receptor–IgG Chimera as a Probe for Adhesive Ligands of Lymph Node High Endothelial Venules," *J. Cell Biol.* 110:2221–2229.

Woodruff, J.J., et al., (1987) "Specific Cell–Adhesion Mechanisms Determining Migration Pathways of Recirculating Lymphocytes," *Ann. Rev. Immunol.* 5:201–222.

Yang, X.-D., et al., (1993) "Inhibition of Insulitis and Prevention of Diabetes in Nonobese Diabetic Mice by Blocking L–selectin and Very Late Antigen 4 Adhesion Receptors," *Proc. Natl. Acad. Sci.* 90:10494–10498.

Yednock, T.A., and Rosen, S.D., (1989) "Lymphocyte Homing," *Adv. Immunol.* 54:313–378.

Yeun, C.T., et al., (1994) "Sulfated Blood Group Lewis$^a$,"*J. Biol. Chem.* 269:1595–1598.

Singh et al. *J. Chem. Soc., Chem. Commun.* 1994, 775–776.

Santos–Benito et al. *J. Exp. Med.* Sep. 1992, 176, 915–918.

Manning et al. *J. Org. Chem.* Oct. 6, 1995, 60, 6254–6255.

Manning et al. "Abstracts of Papers, Part 2", Abstract Number ORGN 61, 206th American Chemical Society National Meeting, Chicago, IL, Aug. 22–27, 1993.

FIG. 1
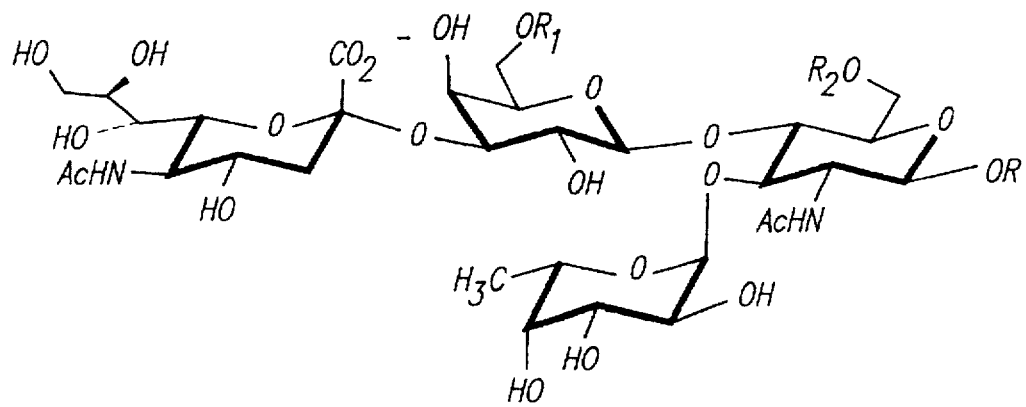
1: $R_1 = R_2 = H$, sialyl Lewis x (sLe$^x$)
2: $R_1 = SO_3^-$, $R_2 = H$, 6'-sulfo sLe$^x$
3: $R_1 = H$, $R_2 = SO_3^-$, 6-sulfo sLe$^x$
4: $R_1 = R_2 = SO_3^-$, 6',6-disulfo sLe$^x$
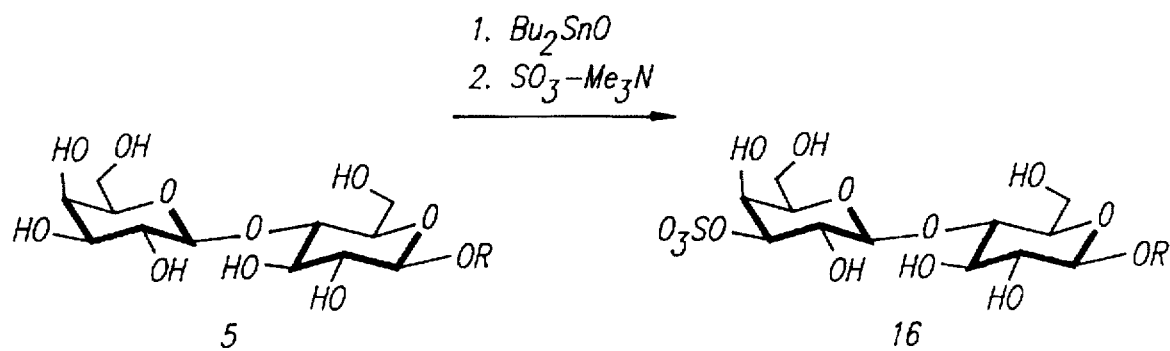
FIG. 4

5,783,693

METHODS FOR SYNTHESIZING SULFATED DISACCHARIDE INHIBITORS OF SELECTINS

CROSS-REFERENCE TO RELATED APPLICATIONS

This application is a continuation-in-part of application Ser. No. 08/432,849, filed May 2, 1995, now U.S. Pat. No. 5,489,578, which is a continuation of patent application Ser. No. 08/155,947, filed Nov. 10, 1993 (now abandoned), both of which applications are incorporated herein by reference and to which applications we claim priority under 35 USC §120.

STATEMENT AS TO FEDERALLY SPONSORED RESEARCH

This invention was made in part with Government support under grant number GM-23547 awarded by the National Institute of Health. The Government may have certain rights in this application.

FIELD OF THE INVENTION

The present invention relates to sulfated carbohydrate ligands which bind to selectin receptors. In particular, this invention relates to synthetic ligands in the form of sulfated disaccharide compounds which inhibit the binding of a selectin receptor to its physiological ligand, including GlyCAM-1, and methods for synthesizing the sulfated disaccharides.

BACKGROUND OF THE INVENTION

Specialized cell surface receptors (termed here selectins) on endothelial cells and various circulating cells are involved in a number of intercellular interactions. For instance, an adhesion molecule on the surface of leukocytes, lymphocyte homing receptor (LHR), is known to be involved in the adhesive interactions of leukocytes with the endothelial lining of blood vessels. This adhesive interaction is a prerequisite for the movement of leukocytes from the blood to tissue sites where immune reactions and inflammatory reactions occur.

LHR is a lectin-like protein which performs its adhesive function recognizing carbohydrate-containing ligands on endothelial cells. Lectin-like receptors have also been found on endothelial cells and platelets. Endothelial leukocyte adhesion molecule-1 (ELAM-1) also known as CD62E and E-selectin is present on endothelial cells and is involved in the recognition of various circulating cells by the endothelium. Granule membrane protein-140 (GMP-140) also known as CD62P and P-selectin is present on the surface of platelets and endothelial cells, where it mediates platelet-leukocyte and endothelium-leukocyte interactions.

Recent work has established that these receptors share certain structural features. Each of the receptors in this class is a glycoprotein with a lectin-like domain, a region with homology to epidermal growth factor, and a region with homology to complement regulatory proteins (see, Springer (1989) Nature 346:425, which is incorporated herein by reference). The term "selectin" is used herein to refer to this class of lectin-like receptors.

There is currently an interest in developing highly specific competitive inhibitors of selectin-mediated cellular adhesion. Such inhibitors are useful in therapeutic regimens to treat various selectin-mediated disease responses. The inhibitors could also be used to target other pharmaceutical compounds, such as anti-inflammatory agents or antioxidants, to the sites of injury.

The broad participation of the selectins in inflammatory disease (Rosen & Bertozzi (1994) Curr. Op. Cell Biol. 6:663–673) has stimulated tremendous interest in the nature of their carbohydrate ligands as leads for the development of anti-inflammatory agents. All three selecting share a common recognition motif, the sialyl Lewis x (sLe$^x$, NeuAcα2,3galβ1,4 (fucα1,3)glcNAc) (FIG. 1) and the related sialyl Lewis a (sLe$^a$, NeuAcα2,3galβ1,3-(fucα1,4)glcNAc) tetrasaccharides (Feizi (1993) Curr. Op. Struct. Biol. 3:701–710; Varki (1994) Proc. Natl. Acad. Sci. USA 91:7390–7397). Sialylation and fucosylation of the core N-acetyllactosamine disaccharide are essential for conferring binding activity. Although the interaction of the selectins with sLe$^x$ oligosaccharides is fairly weak, with equilibrium dissociation constants in the millimolar range (Cooke et al. (1994) Biochemistry 33:10591–10596; Jacob et al. (1995) Biochemistry 34:1210–1217), sLe$^x$ has proven to be an effective antagonist of selectin-mediated adhesion in several animal models of acute inflammation (Mulligan et al. (1993a) J. Exp. Med. 178:623–631; Mulligan et al. (1993b) Nature 364:149–151; Buerke et al. (1994) J. Clin. Invest. 93:1140–1148; Seekamp et al. (1994) Am. J. Pathol. 144:592–598).

Two central problems in the development of sLe$^x$ derivatives as anti-inflammatory agents are the lack of an inexpensive and expedient synthesis, and the susceptibility of the sialic acid and fucose residues to enzymatic cleavage in the bloodstream (Uchiyama et al. (1995) J. Am. Chem. Soc. 117:5395–5396). The chemical syntheses of sLe$^x$ are laborious, involving difficult glycosylation reactions with sialic acid and fucose (Nicolaou et al. (1991) J. Chem. soc., Chem. Commun. 870–872; Nicolaou et al. (1992) J. Am. Chem. Soc. 114:3126–3128; Danishefsky et al. (1992a) J. Am. Chem. Soc. 114:8329–8331; Danishefsky et al. (1992b) J. Am. Chem. Soc. 114:8331–8334; Yoshida et al. (1993) Glycoconjugate J. 10:3–15; Stahl et al. (1994) Angew. Chem. Int. Ed. Engl. 33:2096–2098). The enzymatic synthesis of sLe$^x$ is more efficient, but requires the use of enzymes and cofactors that are either not generally available or very expensive (Dumas et al. (1991) Bioorg. Med. Chem. Lett. 1:425–428; Ichikawa et al. (1992) J. Am. Chem. Soc. 114:9283–9898; Ball et al. (1992) J. Am. Chem. Soc. 114:5449; de Vries et al. (1993) FEBS Lett. 330:243–248; Palcic (1994) Meth. Enzymol. 230:300–316). These difficulties have prompted several groups to explore sLe$^x$ mimetics with reduced structural complexity, and with functional alternatives to sialic acid and fucose. For example, Chen et al. (1994) J. Biol. Chem. 269:1595–1598 and Brandley et al. (1993) Glycobiology 3:633–639, have demonstrated that replacement of sialic acid in sLe$^x$ with a sulfate ester results in equivalent or enhanced selectin binding activity. Uchiyama et al. (1995) supra, have incorporated the essential hydroxyl groups and anionic character of sLe$^x$ into simplified mimetics with equivalent E-selectin binding activity. Finally, a non-carbohydrate-based sLe$^x$ mimetic was designed based on the computer-identified structural similarity of a non-carbohydrate natural product (Rao et al. (1994) J. Biol. Chem. 269:19663–19666). See, also, U.S. Pat. No. 5,428,025, showing that N-acetyllactosamine ligands which bind to endothelial leukocyte adhesion molecule-1 (ELAM-1) are useful in relieving ELAM-1-mediated inflammation.

SUMMARY OF THE INVENTION

The present invention provides novel sulfated disaccharide compounds characterized by their ability to inhibit the binding of any of the known natural selectin receptors to their natural ligand. The sulfated disaccharide compounds are derived from the disaccharide lactose, composed of the O-linked saccharide units galactose and glucose, and are specifically mono-, di-, or tri-sulfated. The compounds of the invention are synthetic molecules which differ from known selectin ligands in lacking sialyl and/or fucosyl moieties.

Accordingly, in one aspect, the invention features a compound having the general formula

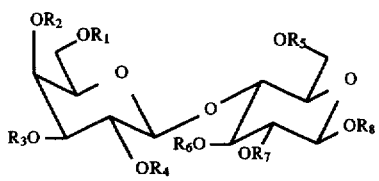

wherein $R_1$ and $R_5$ are each independently H or $SO_3$; $R_2$, $R_4$, $R_6$, and $R_7$ are each independently H, an alkyl group, an acyl group, or fucose; $R_3$ is $SO_3$, H, an alkyl group, or an acyl group; and $R_8$ is an alkyl group, an acetyl group, a acetic acid derivative group, or linkage to a conjugate moiety (which may be a pharmaceutically active drug or a detectable marker), wherein said compound is characterized by its ability to inhibit the binding of a naturally occurring or recombinantly produced selectin receptor to its ligand.

The term "alkyl" means any moiety having the general structure $-(CH_2)_n CH_3$, wherein n is a positive integer of from 0 to 20, and preferably is 0 to 6. The term "acyl" means any moiety having the general structure

wherein R is a carbon atom chain having 1–20 linear or branched carbon atoms. By the term "acetic acid derivative" is meant any moiety having the general structure

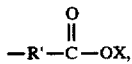

wherein R' is a covalent bond or any organic moiety connected at the appropriate position of the general structure shown above, or preferably an alkyl group, and X is H, an alkyl group, or a metal. The term "acetyl" means a two carbon group containing a methyl group and a carbonyl group, e.g.,

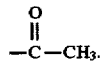

Specific embodiments of the sulfated disaccharide compounds of the invention include lactose 6'-sulfate (lac 6'S), lactose 3'-sulfate (lac 3'S), lactose 3',6'-disulfate (lac 3'6'diS), lactose 6'6-disulfate (lac 6',6diS), and lactose 3',6', 6-trisulfate (lac 3',6',6 triS).

The sulfated disaccharides of the invention can also be used as chimeric molecules conjugated to a chemical moiety such as a peptide, protein, lipid, saccharide, oligosaccharide, polymer, insoluble particle or bead, etc. Such conjugate molecules are produced by binding the molecule to the linking group $R_8$ and can be used to target the compound to a specific site in the body, to enhance bioavailability or other desirable characteristics.

The present invention features methods for efficiently synthesizing the sulfated disaccharides of the invention from inexpensive materials. The methods of the invention overcome prior art synthesis problems by eliminating the need of using sialylated and fucosylated oligosaccharides.

Accordingly, in one aspect, lactose 6'-sulfate (cal 6'S, FIG. 2, 9) and lactose 3',6'-disulfate (lac 3',6'-dis, FIG. 2, 10) are synthesized by (a) selective protection of the 6'-hydroxyl group of 1-β-o-allyl lactose by stannylene-mediated silylation with tert-butyldimethylsilyl chloride (TBDPSCl),(b) protection of the 3'- and 4'-hydroxyl groups with p-methoxybenzylidene acetal, (c) protection of the remaining hydroxyl groups 2', 2, 3, and 6, as benzoate esters, (d) removal of TBDPS and benzylidene groups by methanolysis, (e) sulfation of the primary hydroxyl group 6'with $SO_3$-trimethylamine at room temperature to 37° C. to form lac 6'S or lac 3'6'diS, respectively.

In another embodiment of the synthetic method of the invention, lactose 6'6-disulfate (lac 6',6 diS, FIG. 3, 14) and lactose 3',6',6-trisulfate (lac 3',6',6 triS. FIG. 3,15) are formed from 1-β-o-allyl lactose by (a) selective protection of the 6'- and 6-hydroxyl groups with TBDPSCl, (b) selective protection of the 3'- and 4'-hydroxyl groups with p-methoxybenzylidene acetal, (c) benzoylation of the remaining hydroxyl groups 2', 2, and 3, (d) methanolysis of the tert-butyldimethylsilyl and p-methoxybenzylidene acetal, and (e) sulfation at room temperature or 37° C. to yield lac 6',6-diS, or lac 3',6',6-triS, respectively.

In another embodiment of the synthetic method of the invention, lactose 3'-sulfate (lac 3'S, FIG. 4., 16) is synthesized from 1-β-o-allyl lactose in two steps by reaction with dibutyltin oxide to form the stannylene acetal groups at the 3'- and 4'- hydroxyl groups, followed by sulfation with sulfur trioxide to form lac 3'S.

In one aspect, the invention features sulfated lactose compounds synthesized by the methods of the invention.

The compounds of the invention are therapeutically useful for treating a number of selectin-mediated diseases. The sulfated disaccharides of the invention are selectin antagonists able to prevent binding of selectin to its physiological ligand. Thus, the sulfated disaccharides of the invention are useful as anti-inflammatory therapeutic agents.

In one aspect, the compounds are used in an in vitro assay to determine the presence of selectin receptors in a biological sample. The compound of the invention is attached to a solid support and contacted with a biological sample. Detected binding to the immobilized compound indicates the presence of selectin receptor in the biological sample.

In another aspect, the compounds of the invention are used in an in vivo assay to determine the site of inflammation in a patient. An effective amount of a detectably labeled compound of the invention is administered to a patient. Sufficient time is allowed for the labeled compound to circulate in the patient and attach to selectin. The label and its location is then detected in the patient, indicating the site of inflammation.

These and other objects, advantages and features of the present invention will become apparent to those skilled in the art upon reading this disclosure.

BRIEF DESCRIPTION OF THE DRAWINGS

FIG. 1 is a drawing of the chemical structure of sialyl Lewis* (NeuAcα2,3Galβ1,4(Fucα1,3)GlcNAc), 6'-sulfo sialyl Lewis*, 6-sulfo sialyl Lewis*, and 6'6-disulfo sialyl Lewis*.

FIG. 4 is a flow diagram of the synthesis of lactose 3'-sulfate (lac 3'S, 16).

DETAILED DESCRIPTION

Figure 2:
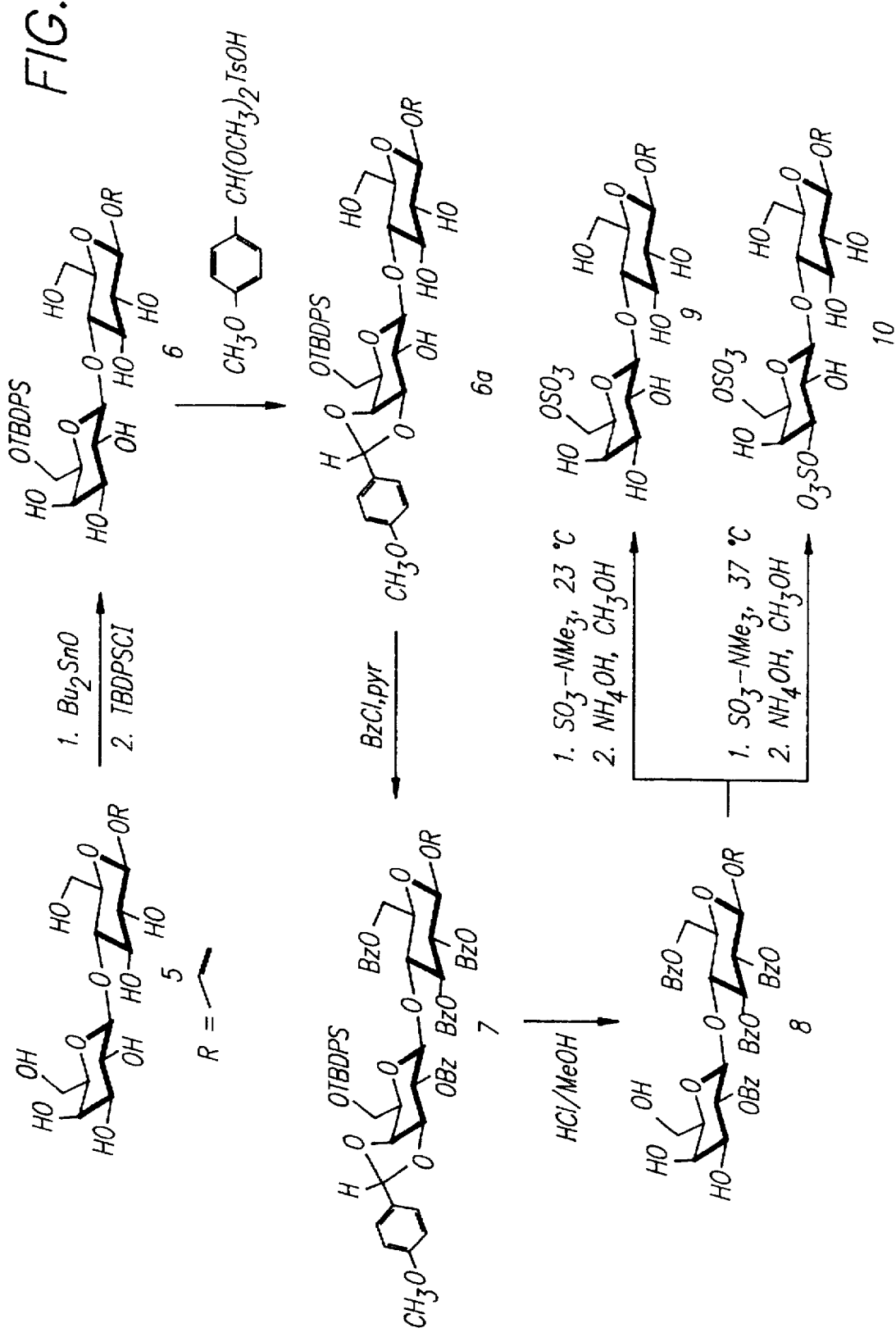
FIG. 2 is a flow diagram of the synthesis of lactose 6'-sulfate (lac 6'S, 9) and lactose 3',6'-disulfate (lac 3'6DiS, 10). Dibutyltin oxide (Bu$_2$SnO), tert-butylmethylsilyl chloride (TBDPSCl), benzoyl chloride (BzCl), pyridine (pyr).

Before the present invention is described, it is to be understood that the terminology used herein is for the purpose of describing particular embodiments only and is not intended to be limiting since the scope of the present invention will be limited only by the appended claims.

It must be noted that as used in this specification and the appended claims, the singular forms "a", "an" and "the" include plural references unless the context clearly dictates otherwise.

Unless defined otherwise all technical and scientific terms used herein have the same meaning as commonly understood by one of ordinary skill in the art to which this invention belongs. Although any methodology and materials similar or equivalent to those described herein can be used in the practice or testing of the present invention, the preferred methods and materials are now described. All publications mentioned herein are incorporated herein by reference for the purpose of disclosing and describing the particular materials and methodologies for which the reference was cited in connection with.

Selectin

The terms "selectin" and "selectin receptor" are used interchangeably herein to broadly encompass molecules of the type described below and their functional equivalents which bind to ligands involved in the inflammatory response. Preferred selectins are L-selectin (CD62L), E-selectin (CD62E) and P-selectin (CD62P), and may be isolated from their natural source or produced by recombinant means.

Selectins, or selectin receptors also known as the "LEC-CAM" family of cell adhesion molecules, are unique cell surface glycoproteins. These receptors are involved in a variety of intercellular interactions. For instance, the trafficking of lymphocytes from the blood into secondary lymphoid organs, such as lymph nodes and gut-associated Peyer's patches, is known to be initiated by an adhesive interaction between specialized endothelial cells of high endothelial venules (HEV) and the lymphocyte homing receptors (LHR) on lymphocytes (Berg et al. (1989) Immunol. Rev. 108:5–18; Duijvestijn & Hamann (1989) Immunol. Today 10:23–28; Woodruff et al. (1987) Ann. Rev. Immunol. 5:201–222; Yednock & Rosen (1989) Adv. Immunol. 54:313–378; Stoolman (1989) Cell 56:907–910; Gallatin et al. (1986) Cell 44:673–680; Rosen (1989) Curr. Opin. Cell. Biol. 1:913–919, all of which are incorporated herein by reference).

LHR (also known as gp90$^{MEL}$, gp100$^{MEL}$, gp110$^{MEL}$, Mel-14antigen, Leu8 antigen, TQ antigen, DREG antigen, LAM-1, selectin 1, LECAM-1, LEC-CAM-1, and L-selectin depending on animal species, leukocyte, and laboratory preference) is expressed on the surface of leukocytes, such as, lymphocytes, neutrophils, monocytes, and eosinophils (Gallatin et al. (1983) Nature 303:30 and Lewinsohn et al. (1987) J. Immunol. 138:4313, which are incorporated herein by reference). LHR is known to mediate the adhesion of lymphocytes to specialized endothelial cells in lymph nodes, leading to the migration of blood-borne lymphocytes into the lymph node. On neutrophils and monocytes, it mediates the early interaction of these cells with endothelium of blood vessels at sites of inflammation.

Therapeutic Use

The sulfated disaccharide compounds of the present invention are particularly useful as selectin antagonists. Antagonists are compounds which partially or completely block the physiological effect of a ligand by partially or completely preventing binding of the ligand to the receptor. An antagonist competes directly or indirectly with the ligand for the receptor binding site and, thus, reduces the proportion of ligand molecules bound to the receptor. Typically, an antagonist will be the topographical equivalent of the natural ligand and will compete directly with the ligand for the binding site on the selectin. Such a compound is referred to here as a "mimetic". A ligand mimetic is a molecule that conformationally and functionally serves as a substitute for the natural ligand recognized by a selectin receptor, i.e., it attaches to the receptor but does not elicit the biological response of the natural ligand. Alternatively, if the ligand and the test compound can bind the receptor simultaneously, the compound may act non-competitively. A non-competitive inhibitor acts by decreasing or inhibiting the subsequent physiological effects of receptor-ligand interactions rather than by diminishing the proportion of ligand molecules bound to the receptor.

The in vivo utility of compounds which block the selectin receptor in the treatment of inflammation has been established. For example, in the cobra venom fraction (CVF) mouse model of lung injury, Mulligan et al. (1994) J. Immunol. 152:832–840 (specifically incorporated by reference), show that systemic administration of an antibody to L-selectin reduced lung injury. In the rabbit ear ischemia-reperfusion model, Mihelcic et al. (1994) Blood 84:2322–2328 (specifically incorporated by reference), show that systemic administration of antibodies to L-selectin significantly decreases tissue injury. In a feline model of myocardial ischemia and reperfusion, Ma et al. (1993) Circulation 88:649–658 (specifically incorporated by reference), show that systemic administration of an L-selectin-blocking agent provides significant cardiovascular protection. In the non-obese (NOD) mouse model, Yang et al. (1993) Proc. Natl. Acad. Sci. 90:10494–10498 (specifically incorporated by reference), show that insulitis and diabetes are inhibited by blocking L-selectin with intraperitoneal injection of anti-L-selectin antibody. These studies support the use of antagonists to L-selectin in the treatment and prevention of acute and chronic inflammation. See also, U.S. Pat. No. 5,428,025, which describes N-acetyllactosamine ligands of ELAM-1 which effectively interrupt its role in acute inflammatory reactions.

The inhibitors of selectin-ligand interaction identified herein are useful in treating a number of selectin-mediated disease responses. For instance, selectins play an important role in recruitment of leukocytes to the sites of injury, particularly inflammation. The inhibitors therefore may be administered locally or systemically to control tissue damage associated with such injuries. Moreover, because of the specificity of such inhibitors for sites of inflammation, these compositions will be more effective and less likely to cause complications when compared to traditional anti-inflammatory agents.

Pharmaceutical compositions comprising the selectin antagonists of the invention can be used to block or inhibit cellular adhesion associated with a number of selectin-mediated disorders. For instance, a number of inflammatory disorders are associated with selectins expressed on vascular endothelial cells and platelets. The term "inflammation" is used here to refer to reactions of both the specific and non-specific defense systems. A specific defense system reaction is a specific immune system reaction to an antigen. Examples of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of PMN leukocytes at sites of bacterial infection (e.g., pulmonary infiltrates in bacterial pneumonias and pus formation in abscesses).

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, septic shock, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma.

Thus, the present invention also provides compounds useful in producing pharmaceutical compositions which can be used in treating the aforementioned conditions. The pharmaceutical compositions can be prepared according to standard methods (see Remington's Pharmaceutical Sciences, Mack Publishing Co., Philadelphia, Pa., 19th ed. (1985) which is incorporated herein by reference). The pharmaceutical compositions are suitable for use in a variety of drug delivery systems. For a brief review of present methods for drug delivery, see, Langer, Science 249:1527–1533 (1990), which is incorporated herein by reference.

In one embodiment, the inhibitors can be used as to target anti-inflammatory drugs or other agents to specific sites of tissue injury. (See U.S. Pat. No. 5,211,937 incorporated by reference). By using a selectin-binding moiety to target a drug to a selectin receptor on, e.g., a vascular endothelial cell, such drugs can achieve higher concentrations at sites of injury. Side effects from the conventional anti-inflammatory agents can be substantially alleviated by the lower dosages, the localization of the agent at the injury sites and/or the encapsulation of the agent prior to delivery. Targeting can be achieved by directly or indirectly linking the inhibitor to the anti-inflammatory agent. For instance, liposomes filled with the anti-inflammatory agent can be constructed which incorporate the inhibitor in the lipid membrane (see, Langer, supra). When the liposomes are brought into proximity of the affected cells, they deliver the elected therapeutic compositions.

The pharmaceutical compositions containing the inhibitors can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Amounts effective for this will, of course, depend on the severity of the disease and the weight and general state of the patient.

In prophylactic applications, compositions containing the inhibitors are administered to a patient susceptible to or otherwise at risk of a particular disease. Such an amount is defined to be a "prophylactically effective dose." In this use, the precise amounts again depend on the patient's state of health and weight.

The sulfated disaccharides of the invention are preferably administered with a pharmaceutically acceptable carrier, the nature of the carrier differing with the mode of administration, for example, oral administration, usually using a solid carrier and I.V. administration a liquid salt solution carrier.

The desired formulation can be made using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the sulfated disaccharides of the invention directly in transdermal formulations with permeation enhancers such as DMSO. Other topical formulations can be administered to treat dermal inflammation.

A therapeutically effective amount is an amount of sulfated disaccharide molecule which will bind to a substantial proportional number of selectin receptor molecules so that a selectin-mediated disorder, e.g., inflammation, can either be prevented or ameliorated. Thus, "treating" as used herein shall mean preventing or ameliorating a selectin-mediated disorder and/or symptoms associated with the disorder. Typically, the compositions of the instant invention will contain from less than 1% to about 95% of the active ingredient, preferably about 10% to about 50%. Preferably, between 10 mg and 50 mg will be administered to a child and between 50 mg and 1000 mg will be administered to an adult. The frequency of administration will be determined by the care provider based on patient responsiveness. Other effective dosages can be readily determined by one of ordinary skill in the art through routine trials establishing dose response curves.

In determining the dose of sulfated disaccharide to be administered, it must be kept in mind that one may not wish to completely block all of the selectin receptors. In order for a normal healing process to proceed, at least some of the white blood cells or neutrophils must be brought into the tissue in the areas where the wound, infection or disease state is occurring. The amount of the sulfated disaccharide administered as blocking agents must be adjusted carefully based on the particular needs of the patient while taking into consideration a variety of factors such as the type of disease that is being treated.

It is believed that the compounds of the present invention can be used to treat a wide range of diseases, including diseases such as rheumatoid arthritis, asthma, adult respiratory distress syndrome, sarcoidosis, hypersensitivity pneumonitis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of sulfated disaccharides might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The white blood cells possess the L-selectin or LECAM-1 receptor. The receptors adhere to ligand molecules on the surface of activated endothelial cells. The ligand molecules may be induced to the surface of the endothelial cells by activation. Large numbers of white blood cells are quickly captured and brought into the tissue surrounding the affected area, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. This is most preferably done by local injection of the sulfated disaccharides of the invention to the area subjected to trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the sulfated disaccharides of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A variety of different respiratory diseases exhibit symptoms which are aggravated by inflammation and all aspects of the present invention can be used in the treatment of such diseases in order to alleviate and/or prevent the aggravation of such symptoms. This is preferably done by the topical pulmonary administration of the sulfated disaccharides of the invention. Such compounds can be topically delivered to the passages of the lung surface. Aerosol formulations may be delivered by the use of conventional metered dose inhalers (MDIs). By formulating any or all of the sulfated disaccharides in combination with a suitable propellant and delivering the formulation via an MDI, relief from pulmonary inflammation can be obtained in a very short period of time.

Sulfated disaccharides of the invention are preferably administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the 5 art. See, e.g., Remington's Pharmaceutical Sciences, supra. The composition or formulation to be administered will, in any event, contain a quantity of the sulfated disaccharide adequate to achieve the desired state in the subject being treated.

The various sulfated disaccharides of the present invention can be used by themselves, with each other, or in combination with pharmaceutically acceptable excipient materials as described above. Further, the sulfated disaccharide compounds of the invention can be made as conjugates wherein the sulfated disaccharides are linked in some manner to a label, e.g., fluorescent, radioactive and enzyme labels. By forming such conjugates, the compounds of the invention act as biochemical delivery systems for the label so that a site of inflammation can be detected.

The sulfated disaccharides of the invention can also be used as chimeric molecules conjugated to a chemical moiety such as a peptide, protein, lipid, saccharide, oligosaccharide, polymer, etc. Such conjugate molecules can be used to target the compound to a specific site in the body, to enhance bioavailability or other desirable characteristics.

Sulfated disaccharides of the invention could also be used as laboratory probes to test for the presence of a selectin in a sample. Such probes are preferably labeled with a detectable marker, e.g., a radioactive or fluorescent label.

The compounds of the invention are useful in an in vitro assay to determine the presence of selectin receptors in a biological sample. The compound of the invention is attached to a solid support and contacted with a biological sample. Detected binding to the immobilized compound indicates the presence of selectin receptor in the biological sample.

The compound may be labeled, e.g., radioactive or fluorescently tagged, and mixed with a sample to be tested. The binding of the labeled sulfated disaccharide compound is then determined by methods known to those skilled in the art. Determination of bound label thus indicates the presence of selectin in the biological sample. Such an assay may also be used to quantitate selectin in a biological sample.

The disaccharide compound of the invention is also useful in vivo to locate a site of inflammation. An effective amount of the labeled sulfated disaccharide compound of the invention is administered to a patient, and sufficient time allowed for the compound to circulate in the patient and attach to selectin in the patient. The location of the label is then detected in the patient, and thus the site of inflammation is determined.

Selectin Antagonists

The new selectin antagonists disclosed herein were designed based in part on characterization of the biological macromolecules that support selectin adhesion in vivo. Accumulating evidence suggests that each selectin binds to a discrete glycoprotein ligand or set of ligands on cognate cells, and that features unique to these ligands confer selectin specificity (Rosen & Bertozzi (1994) Curr. Op. Cell Biol. 6:663–673). Three HEV-associated ligands for L-selectin have previously been identified as mucin-like glycoproteins: GlyCAM-1 (Lasky et al. (1992) Cell 69:927–938 ), CD34 (Baumheuter et al. (1993) Science 262:436–438) and MAdCAM-1 (Briskin et al. (1993) Nature 363:461–464). Discrete physiological ligands for P-selectin (PSGL-1) (Norgard et al. (1993) J. Biol. Chem. 268:12764–12774; Sako et al. (1993) Cell 75:1179–1186) and E-selectin (ESL-1) (Steegmaier et al. (1995) Nature 373:615–620) on myeloid cells have also been described. Presumably, these glycoproteins present the proper carbohydrate-based epitopes for optimal selectin binding in vivo.

GlyCAM-1 is the best characterized among the three known L-selectin ligands and, as a secreted component that is present in serum, may function as a signaling molecule that acts through L-selectin. GlyCAM-1 is modified with dense clusters of sulfated and sialylated o-linked oligosaccharide chains. Sulfation and sialylation are crucial for high-avidity binding to L-selectin (Imai et al. (1993) Nature 361:555–557; Crommie & Rosen (1995) J. Biol. Chem., In Press).

A detailed structural analysis of these sulfated oligosaccharides was performed, revealing two novel structures: NeuAcα2-3(6-SO$_3$)gal β1-4(fucα1-3)glcNAc (6'-sulfo sLe$^x$) and NeuAcα2-3galβ1-4(fucα1-3) (6-SO$_3$)glcNAc (6-sulfo sLe$^x$) (Hemmerich et al. (1994) Biochemistry 33:4820–4829); Hemmerich & Rosen (1994) Biochemistry 33:4830–4835; Hemmerich et al. (1995) J. Biol. Chem. 270:12035–12047). 6',6-Disulfo sLe$^x$ is also thought to be a determinant on GlyCAM-1. Based on the known sulfation requirement for L-selectin binding to GlyCAM-1, it has been proposed that the sulfate esters of these enhance the affinity of sLe$^x$ for L-selectin. Indeed, Scudder et al. (1994) Glycobiology 4:929–933 have recently reported that 6-sulfo sLe$^x$ shows enhanced in vitro L-selectin binding activity compared to sLe$^x$.

Using these observations, a strategy was developed for the generation of simple small molecules with L-selectin binding activity. It was reasoned that the incorporation of sulfate esters at key positions on a core disaccharide impart binding activity for L-selectin without need for sialylation or fucosylation. The sulfated disaccharide compounds of the invention where synthesized, and their relative L-selectin binding activities determined. The compounds were assayed using a novel inhibition ELISA based on the binding of L-selectin to GlyCAM-1, disclosed in patent application Ser. No. 08/425,362, herein specifically incorporated by reference. This assay enables the direct comparison of the inhibitory activities of different compounds, in contrast to previously described direct binding assays which potentially suffer from variation in the packing density of the immobilized lipid-linked substrates.

The compounds of the invention are encompassed by the compound having the general structural feature:

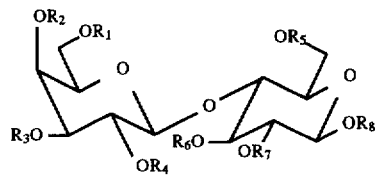

wherein $R_1$ and $R_5$ are each independently H or $SO_3$; $R_2$, $R_4$, $R_6$, and $R_7$ are each independently H, alkyl, an acyl group, or fucose; $R_3$ is $SO_3$, H, alkyl, or an acyl group; and $R_8$ is an alkyl group, an acetyl group, a acetic acid derivative group, or linkage to a conjugate moiety (which may be a pharmaceutically active drug or a detectable marker), wherein said compound is characterized by its ability to inhibit the binding of a naturally occurring or recombinantly produced selectin receptor to its ligand.

Generally, $R_1$–$R_8$ are defined so at least one group is $SO_3$. More preferably, $R_1$, $R_3$, and $R_5$ are each independently H or $SO_3$, $R_2$, $R_4$, $R_6$, and $R_7$ are H, and $R_8$ is a linking group covalently bound to a pharmaceutically active drug or detectable label. Specifically preferred embodiments of the sulfated disaccharide compounds of the invention include lactose 6'-sulfate (lac 6'S), lactose 3'-sulfate (lac 3'S), lactose 3',6'-disulfate (lac 3'6'diS), lactose 6'6-disulfate (lac 6',6 dis), and lactose 3',6',6-trisulfate (lac 3',6',6triS).

Lactose 6'-sulfate (lac 6'S, 9) and lactose 3',6'-disulfate (lac 3',6'diS, 10) were synthesized as described in Example 1 below. An efficient synthetic strategy was designed to provide several sulfated disaccharides from a minimal set of precursor molecules. Lactose β-allyl glycoside (galβ1, 4glcβ1-OAll, 5, FIG. 2) was chosen as a readily available core disaccharide based on the observation that replacement of glcNAc by glucose in sLe$^x$ has no detrimental effect on selectin binding activity (Nelson et al. (1993) J. Clin. Invest. 91:1157–1166). In addition, the allyl group allows facile conjugation to lipids, proteins or other scaffolds. Selective protection of the 6'-hydroxyl group of 5 was achieved by stannylene-mediated silylation with tert-butyldiphenylsilyl chloride (TBDPSCl), as described by Leigh and coworkers, to afford compound 6 (Glen et al. (1993) Carbohydr. Res. 248:365–369). The 3'- and 4'-hydroxyl groups were protected as the p-methoxybenzylidene acetal, and the remaining hydroxyl groups were protected as benzoate esters (7). Removal of the TBDPS and benzylidene groups by methanolysis (Nashed & Glaudemans (1987) J. Org. Chem. 52:5255–5260) gave compound 8, which could accept sulfate esters on the 6'- and 3'-positions. Treatment of compound 8 with $SO_3$-trimethylamine complex at room temperature resulted in sulfation at the primary hydroxyl group (6') with good selectivity, affording, after deprotection, lac 6'S (9). When the temperature of the sulfation reaction was increased to 37° C., disulfate 10 was formed with good selectivity. In this reaction, the equatorial 3'-hydroxyl group is sulfated preferentially over the less reactive axial 4'-hydroxyl group.

Figure 3:
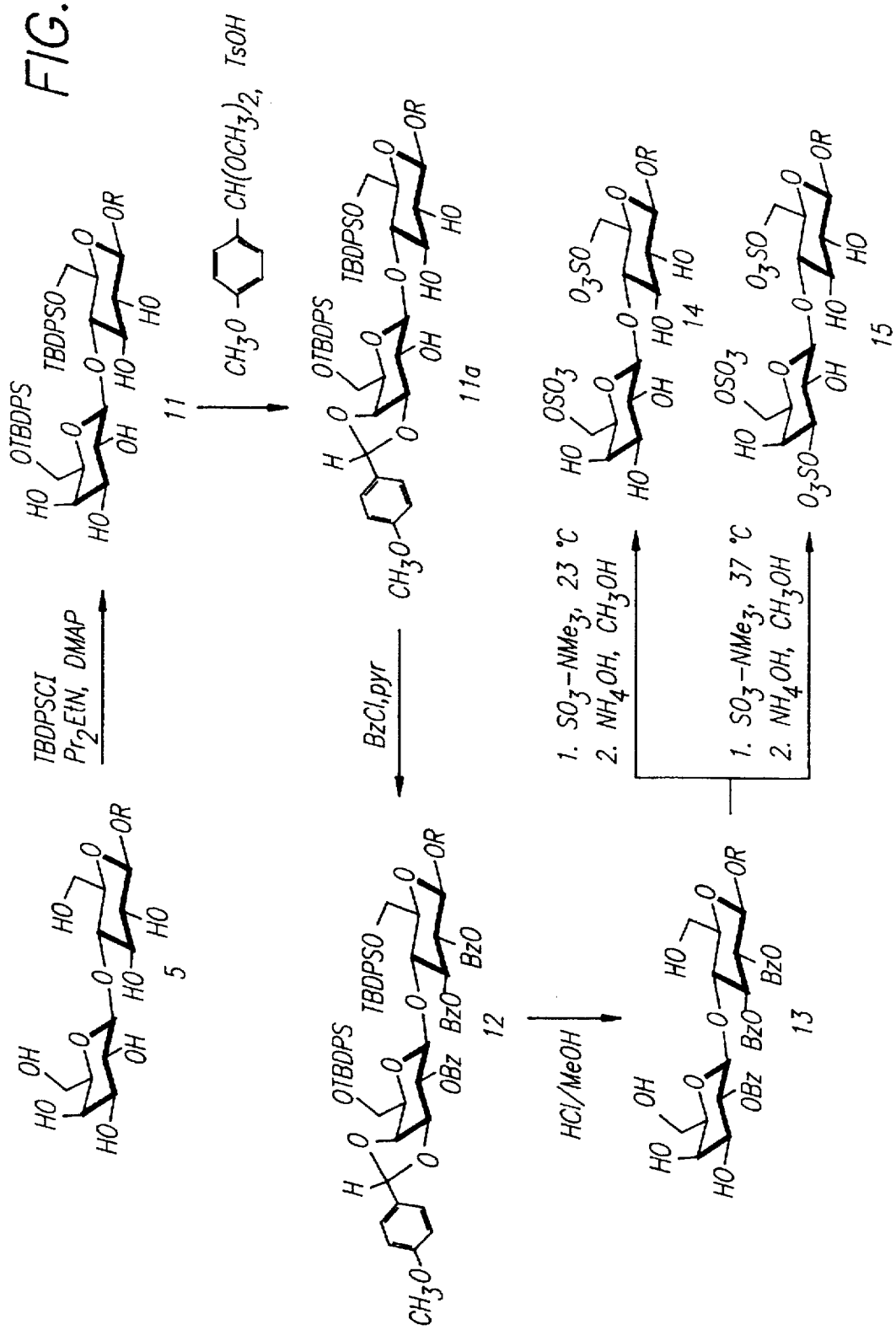
FIG. 3 is a flow diagram of the synthesis of lactose 6',6-disulfate (lac 6'6 diS, 14) and lactose 3',6',6-trisulfate (lac 3'6 DiS, 15). Dibutyltin oxide (Bu$_2$SnO), tert-butyldimethylsilyl chloride (TBDPSCl), benzoyl chloride (BzCl), pyridine (pyr), diisopropylethylamine (Pr$_2$EtN), dimethylaminopyridine (DMAP).

A related strategy was applied to the synthesis of lactose 6',6-disulfate (lac 6'6 diS, 14) and lactose 3',6',6trisulfate (lac 3'6'6 tris, 15) (FIG. 3). Selective protection of the 6'- and 6-hydroxyl groups of 5 with TBDPSCl yielded compound 11. Selective protection of the 3'- and 4'-hydroxyls followed by benzoylation of the remaining hydroxyl groups provided compound 12, which was subjected to methanolysis to give the selectively protected derivative 13. Sulfation of 13 at room temperature followed by deprotection gave lac 6'6 diS (14) with good selectivity, while sulfation at 37° C. and deprotection gave lac 3'6'6 tris (15). Finally, lactose 3'-sulfate (lac 3'S, 16) was synthesized in two steps from 5 by stannylene-directed sulfation with $SO_3$-trimethylamine (FIG. 4) (Alias et al. (1983) Tet. Lett. 24:2383–2386; Lubineau & Lemoine (1994) Tet. Lett. 35:8795–8796).

Figure 5:
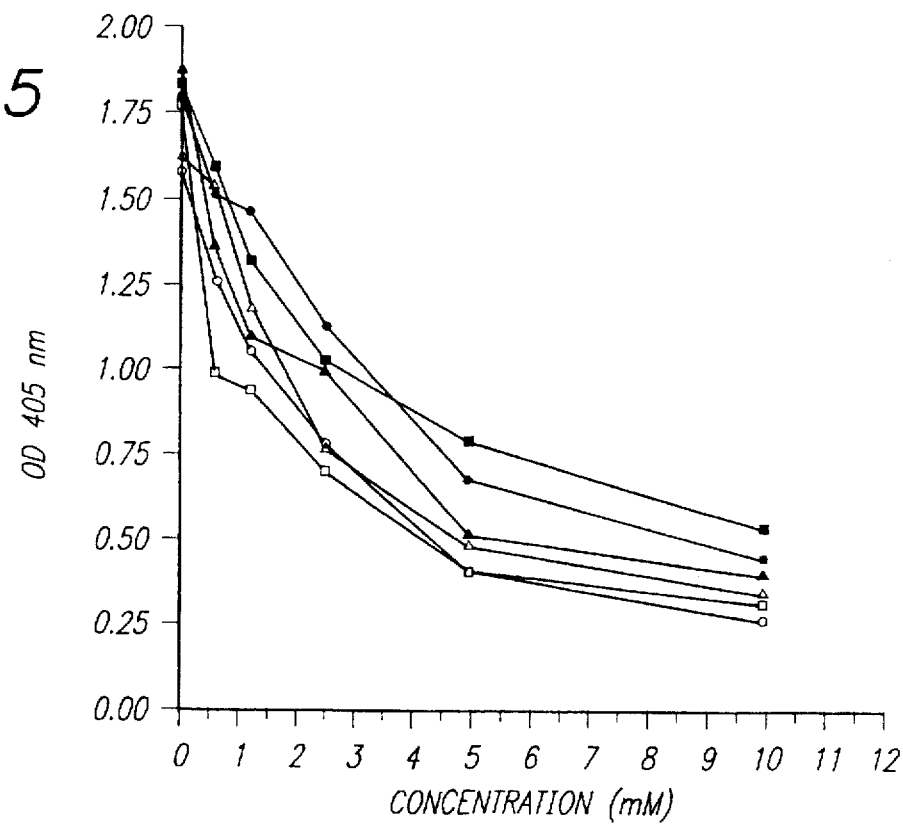
FIG. 5 is a diagram of the inhibition of L-selectin-IgG binding to GlyCAM-1 by sulfated disaccharides: lactose 6'-sulfate (lac 6'S) (■), lactose 3'-sulfate (lac 3'S) (●), lactose 3',6'-disulfate (lac 3'6'diS) (▲), lactose 6',6-disulfate (lac 6'6 diS) (□), lactose 3',6'6-trisulfate (lac 3'6'6 triS) (○) and M6P (△). The maximal concentration tested was 10 mM, followed by 2-fold serial dilutions. The concentrations required for 50% inhibition (IC$_{50}$) were calculated using a value for 100% inhibition derived from the amount of bound L-selectin-IgG in the presences of 20 mM M6P.

Compounds 9, 10, 14, 15 and 16 were tested as inhibitors of the binding of a recombinant L-selectin-IgG chimera (Watson et al. (1990) J. Cell Biol. 110:2221–2229) to immobilized GlyCAM-1 in an ELISA (Example 4). This assay is described in co-pending patent application Ser. No. 08/425,362, filed Apr. 18, 1995, which is specifically incorporated herein. The synthetic compounds were compared to the known L-selectin-binding carbohydrates $sLe^x$, $sLe^a$ and mannose-6-phosphate (M6P) (Imai et al. (1992) Glycobiology 2:373–381). The concentrations required for 50% inhibition ($IC_{50}$) were all found to be in the low millimolar range (0.8–4 mM), yet significant differences in potency were observed (FIG. 5).

Figure 6:
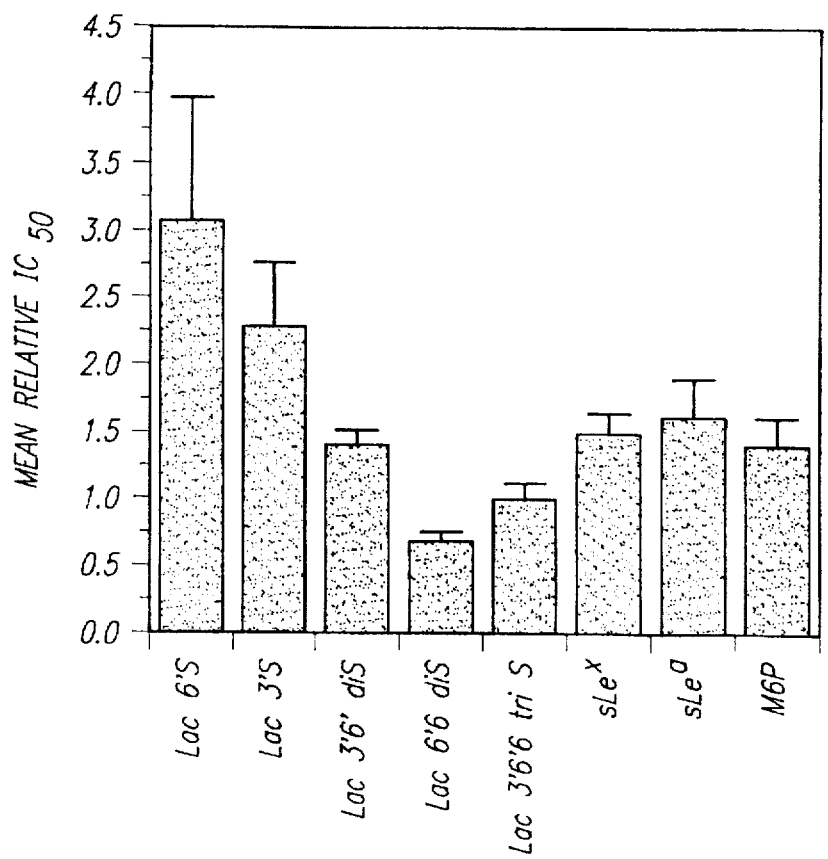
FIG. 6 is a bar graph showing the mean relative IC$_{50}$ values for synthetic lactose sulfates and comparison compounds. IC$_{50}$ values obtained in each experiment were normalized, and lac 3'6'6 triS assigned a value of 1.0. Mean relative IC$_{50}$ values were calculated for each compound (standard error represented by error bars). The error associated with the mean relative IC$_{50}$ of lac 3'6'6 tris were normalized to those for lac 6'6 diS in each experiment. A standard error of the mean was calculated and scaled to the assigned mean relative IC$_{50}$ value for lac 3'6'6 triS. The significance of differences in mean relative IC$_{50}$ values were evaluated using the two-tailed Student t-test: lac 6'S v. lac 3'6'diS ($p<0.14$); lac 3'S v. lac 3'6'diS ($p<0.15$); lac 3'6'diS v. lac 6'6 diS ($p<0.0018$); lac 6'6 diS v. sLe$^x$ ($p<0.0048$); lac 6'6 diS v. sLe$^a$ ($p<0.0073$).

In order to compare data from several experiments, $IC_{50}$ values were normalized for each experiment, with lac 3'6'6 triS being assigned a value of 1.0. FIG. 6 shows the mean relative $IC_{50}$ values obtained from several experiments. The statistical significance of differences in relative $IC_{50}$ were evaluated by application of the two-tailed Student t-test to pairs of data sets.

Although the parent disaccharide lactose shows no inhibitory activity at a concentration of 10 mM (not shown), the addition of one sulfate ester at either the 6'- (lac 6'S, 9) or 3'-position (lac 3'S, 16) confers weak but measurable binding activity. The relative $IC_{50}$ values for lac 6'S and lac 3'S were 2.2 and 1.6-fold higher, respectively, than that of lac 3'6'diS (10).

When sulfate esters were simultaneously present at the 6'- and 6-positions, the resulting derivative (lac 6'6diS, 14) was 3–5 times more potent than the monosulfates ($p<0.029$ for lac 6'S; $p<0.011$ for lac 3'S), and 2-fold more potent than lac 3'6'diS ($p<0.0018$). Although lac 6'6 diS and lac 3'6 diS are both disulfated, the positions of sulfation are important for dictating inhibitory potency. Notably, lac 6'6 diS was greater than 2-fold more potent than $sLe^x$ ($p<0.0048$) or $sLe^x$ ($p<0.0073$), despite the absence of functionalities corresponding to sialic acid and fucose. $SLe^x$ and $sLe^a$ showed inhibitory activities comparable to M6P.

The presence of an additional sulfate ester at the 3'-position, yielding lac 3'6'6 tris (15), did not enhance the inhibitory potency relative to lac 6'6 diS. This result contrasts with the apparent trend observed with lac 6'S and lac 3'6'diS. It is possible that cooperative interaction of the 6'- and 6-sulfates with L-selectin precludes a favorable, simultaneous interaction with the 3'-sulfate.

These experiments establish that the sulfated disaccharide derivatives of the invention are inhibitors of the binding of L-selectin to the physiologically-relevant ligand GlyCAM-1. Judicious placement of sulfate esters on the lactose backbone, guided by the oligosaccharide structures on GlyCAM-1, results in the generation of a simple molecule (lac 6'6 diS) with greater L-selectin inhibitory potency than $sLe^x$. Unlike $sLe^x$, lac 6'6 diS can be synthesized in only a few steps from an inexpensive disaccharide, and can be easily generated on a large scale. Similar leads in the development of P- and E-selectin inhibitors may derive from a detailed biochemical analysis of their respective physiological ligands.

EXAMPLES

The following examples are put forth so as to provide those of ordinary skill in the art with a complete disclosure and description of how to make the assays, the assay components, and carry out the assays of the invention and are not intended to limit the scope of what is regarded as the invention. Efforts have been made to ensure accuracy with respect to numbers used (e.g., amounts, temperature, etc.) as well as the nomenclature used but some experimental error and deviation should be accounted for. Unless indicated otherwise, parts or parts by weight, molecular weight is weight average molecular weight, temperature is in degree centigrade and pressure is at or near atmospheric.

Example 1

Synthesis of Lactose 6'-sulfate and Lactose 3',6'-disulfate

All reagents were obtained from commercial suppliers and were used without further purification unless otherwise noted. Benzoyl chloride was distilled onto 3 Å molecular sieves/$K_2CO_3$ prior to use. THF was distilled from Na/benzophenone and methylene chloride was distilled from $CaH_2$ immediately prior to use. Methanol and DMF were dried prior to use over 3 Å molecular sieves. $^1H$ NMR spectra were recorded at 300 MHz and $^{13}C$ NMR spectra were recorded at 75 MHz using a General Electric NMR Spectrometer. NMR data are tabulated as chemical shifts in ppm ($\delta$) downfield of tetramethylsilane (0 ppm), followed by multiplicity (s, singlet; d, doublet; t, triplet; app, apparent; br, broad), integration, and coupling constant(s) (J) in Hz. Liquid secondary ion mass spectra (LSIMS) were obtained on a VG-70SE spectrometer at the UCSF Mass Spectrometry Facility.

6'-O-tert-Butyldimethylsilyl-1-β-O-allyl lactose (6). A solution of 0.688 g (1.8 mmol) of 1-β-O-allyl lactose (5) and 0.5 g (2.0 mmol) of dibutyltin oxide in 35 ml of anhydrous methanol was heated at reflux for 9 h in the presence of 3 Å molecular sieves. The solution was cooled to room temperature, filtered through celite and concentrated. The resulting residue was suspended in anhydrous THF under an argon atmosphere, and 520 ml (2.0 mmol) of tert-butyldimethylsilyl chloride was added via syringe. After 24 h, the solution was concentrated and purified by silica gel chromatography eluting with 20:1methylene chloride/methanol to afford 0.789 g (71%) of a white solid. Only one product was detected by NMR analysis; $^1H$ NMR ($CD_3OD$) $\delta$0.98 (2, 9 H), 3.183 (app t, 1 H, J=8.4), 3.35 (m, 1 H), 3.40–3.53 (m, 4 H), 3.59 (app t, 1 H, J=6.5), 3.75–3.83 (m, 4 H), 4.06 (dd, 1 H, J=12.8, 5.9), 4.23–4.31 (m, 4 H), 5.08 (dd, 1 H, J=10.3, 1.0), 5.24 (dd, 1 H, J=17.2, 1.0), 5.87 (m, 1 H), 7.31–7.35 (m, 6 H), 7.60–7.65 (m, 4 H); $^{13}C$ NMR $\delta$19.96, 27.34, 61.73, 63.53, 69.66, 71.08, 72.42, 74.77, 76.12, 76.34, 76.59, 80.22, 103.18, 104.92, 117.46, 128.83, 128.89, 130.93, 134.32, 134.38, 135.61, 136.66. The position of silylation (6') was assigned by proton decoupling analysis of the corresponding peracetylated derivative.

6'-O-tert-Butyldimethylsilyl-3',4'-O-p-methoxybenzylidene-1-β-O-allyl lactose (6a). A solution of 0.25 g (0.4 mmol) of compound 6, 205 ml (1.2 mmol) of p-methoxybenzaldehyde dimethyl acetal, and a catalytic amount of p-toluenesulfonic acid in 7 ml of anhydrous DMF was stirred over 4 Å sieves. The solution was heated to 50° C. under aspirator pressure for 9 h, cooled to room temperature and neutralized with triethylamine. The solution was concentrated and the product purified by silica gel chromatography eluting with 60:1 methylene chloride/methanol to afford 0.21 g (71%) of a colorless syrup. The product was obtained as an inseparable mixture of diastereomers (3:1 ratio by $^1$H NMR analysis), which was carried on to the next step without further characterization.

6'-O-tert-Butyldimethylsilyl-3',4'-O-p-methoxybenzylidene-2',2,3,6-tetra-O-benzoyl-1-β-O-allyl lactose (7). Compound 6a (0.625 g, 0.85 mmol, diastereomeric mixture) was dissolved in 10 ml of anhydrous methylene chloride under an argon atmosphere. Diisopropylethylamine (1.47 ml, 8.5 mmol) and pyridine (1.37 ml, 17 mmol) were added via syringe and the solution was cooled to 0° C. Benzoyl chloride (0.98 ml, 8.5 mmol) was added dropwise over a 10-min period, and the solution was warmed to room temperature overnight. The reaction was quenched with a saturated solution of NaHCO$_3$ and then concentrated. The residue was dissolved in ether and washed with water, 0.2M HCl, saturated NaHCO$_3$ and brine. After drying over MgSO$_4$, the solution was concentrated and the product purified by silica gel chromatography eluting with 5:1 hexanes/ethyl acetate to afford 0.99 g (100%) of a white foamy solid. $^1$H NMR analysis indicated a mixture of diastereomer ic?? tetrabenzoates, which was taken on to the next step without further characterization.

2',6,3,2-Tetra-o-benzoyl-1-β-O-allyl lactose (8). A solution of anhydrous HCl in methanol was generated by the addition of 0.4 ml of acetyl chloride to 10 ml of anhydrous methanol under an argon atmosphere. This solution (6 ml) was added to a solution of 0.2 g (0.17 mmol) of compound 7 in 6 ml of anhydrous ether. The reaction was stirred at room temperature for 24 h, and then diluted with ether and washed with water, saturated NaHCO$_3$ and brine. After drying over MgSO$_4$, the solution was concentrated and the product purified by silica gel chromatography eluting with 50:1 methylene chloride/methanol to afford 91 mg (67%) of a white solid; $^1$H NMR (50:1 CDCl$_3$/CD$_3$OD) δ 2.98–3.04 (m, 1H), 3.07–3.13 (m, 1 H), 3.20 (app t, 1 H, J=6.0), 3.58 (dd, 1 H, J=10.0, 3.4), 3.74–3.80 (m, 2 H), 3.98–4.12 (m, 2 H), 4.21 (dd, 1 H, J=13.2, 4.7), 4.44 (dd, 1 H, J=12.0, 4.9), 4.53 (m, 2 H), 4.71 (d, 1 H, J=7.8), 5.03 (app d, 1 H, J=10.4), 5.11 (app d, 1 H, J=17.9), 5.23 (dd, 1 H, J=9.7, 8.3), 5.37 (app t, 1 H, J=9.5), 5.62–5.75 (m, 2 H), 7.26–7.61 (m, 12 H), 7.88–8.02 (m, 8 H).

6'-Sulfo-1β-O-allyl lactose (9). A solution of compound 8 (20.7 mg, 0.026 mmol) and sulfur trioxide-trimethylamine complex (22 mg, 0.052 mmol) in 1 ml of anhydrous DMF was stirred at room temperature. Selective monosulfation of the primary 6'-OH was monitored by anion exchange HPLC (Rainin Hydropore-5-AX, PEI matrix) eluting with a linear gradient of 90% methanol to 1 M NH$_4$OAc in 90% methanol, with detection at 280 nm. After 2.5 h, compound 8was mostly converted to the corresponding monosulfate, with a small amount of disulfate. The reaction was stopped by addition of 250 ml of methanol, followed by purification on a column of Sephadex LH-20 (2.8 ×100 cm) eluting with DMF. The fractions containing the product (detected by thin layer chromatography eluting with 5:3:2 n-butanol/acetic acid/water) were pooled and concentrated. The residue was dissolved in 5 ml of methanol, and combined with 5 ml of aqueous NH$_4$OH (10 M). The solution was heated at 55° C. for 12 h, the insoluble material was filtered, and the filtrate concentrated. The crude deprotected product was purified by anion exchange chromatography on DEAE-sepharose eluting with a linear gradient of 2 mM to 1M pyridinium acetate (pyr-OAc, pH 5), and the fractions were quantified using the phenol-sulfuric acid assay. Fractions containing the monosulfate (eluting at 150–200 mM pyr-OAc) were pooled and lyophilized twice from water. The pyridinium salt was converted to the sodium salt by passage down a column of BioRad AG50W-X4resin (Na$^+$ form) and the eluate was lyophilized to afford 7 mg (55%) of the desired 6'-monosulfate (only one isomer was observed by $^1$H NMR); $^1$H NMR (D$_2$O) δ3.35 (m, 1 H), 3.52–3.71 (m, 5 H), 3.77–3.82 (m, 1 H), 3.96–4.00 (m, 3 H), 4.20–4.26 (m, 3 H), 4.39 (dd, 1 H, J=12.7, 5.7), 4.47 (d, 1 H, J=7.7), 4.54 (d, 1 H, J=8.0), 5.29 (app d, 1 H, J=10.4), 5.38 (app d, 1 H, J=17.0), 5.97 (m, 1 H); MS (LSIMS, negative mode) calcd for C$_{15}$H$_{26}$O$_{14}$S: 462, found: 461 (M-H).

3',6'-Disulfo-1-β-O-allyl lactose (10). A solution of compound 8 (37 mg, 0.046 mmol) and sulfur trioxide-trimethylamine complex (19 mg, 0.138 mmol) was heated at 37° C. for 5 h. The progress of sulfation was monitored by anion exchange HPLC as described for compound 9, and the reaction was stopped by addition of methanol after approximately 50% conversion to the disulfate, the remainder being largely monosulfate with a small amount of trisulfate. Purification by sephadex LH-20 chromatography and deprotection with methanolic NH$_4$OH were performed as described for compound 9. The mixture of deprotected mono- and disulfates was separated by anion exchange chromatography on DEAE-sepharose eluting with a linear gradient of 2 mM to 1M pyr-OAc (pH 5). The monosulfate eluted at 150–200 mM pyr-OAc, and the disulfate eluted at 400–500 mM pyr-OAc. The respective fractions were pooled, twice lyophilized from water, and converted to the corresponding Na$^+$ salts as described for compound 9. The monosulfated product (8 mg, 35% yield) was identical to compound 9, with no other monosulfate isomers detectable by $^1$H NMR. The disulfated product 10 (17 mg, 62%) was also a single isomer by $^1$H NMR. Sulfation at the 3'- and 6'-positions was assigned based on the down-field shifts of the adjacent protons in the $^1$H NMR spectrum; $^1$H NMR (D$_2$O) δ3.34(m, 1 H), 3.62–3.71 (m, 4 H), 3.80, (dd, 1 H, J=12.1, 4.4), 3.96–4.04 (m, 2 H), 4.20–4.25 (m, 3 H), 4.33–4.42 (m, 3 H), 4.53 (d, 1 H, J=8.0), 4.58 (d, 1 H, J=7.9), 5.27 (app d, 1 H, J=10.4), 5.37 (app d, 1 H, J=16.2), 5.97 (m, 1 H); MS (LSIMS, negative mode) calcd for C$_{15}$H$_{26}$O$_{17}$S$_2$: 542; found 563(M-2H+Na).

Example 2

Synthesis of Lactose 6',6-disulfate and Lactose 3', 6',6 trisulfate

6',6-Di-O-tert-butyldimethylsilyl-1-β-O-allyl lactose (11). To a solution of 1-β-O-allyl lactose (5) (0.5 g, 1.3 mmol) in 4 ml of anhydrous DMF were added diisopropylethylamine (905 ml, 5.2 mmol), dimethylaminopyridine (32 mg, 0.26 mmol), tert-butyldimethylsilyl chloride (748 ml, 2.9 mmol) and 3 Åmolecular sieves. The solution was stirred for 10 h at room temperature, quenched with methanol and concentrated. The residue was dissolved in methylene chloride, washed three times with water, once with 0.1M HCl and once with saturated NaHCO$_3$. The organic layer was dried over MgSO$_4$, and the product was purified by silica gel chromatography eluting with 4:1 ethyl acetate/hexanes to afford 0.46 g (43%) of a white solid; $^1$H NMR (CDCl$_3$) δ1.05 (s, 18 H), 2.57(s, 1 H), 2.73 (s, 1 H), 2.85 (s, 1 H), 2.87 (s, 1 H), 2.95 (s, 1 H), 3.35–3.69 (m, 6 H), 3.83–4.11 (m, 6 H), 4.24–4.40 (m, 4 H), 5.21 (app d, 1 H, J=10.1), 5.31 (app d, 1 H, J=17.1), 5.95 (m, 1 H), 7.50 (m, 12 H), 7.66–7.74 (m, 8 H); $^{13}C$ NMR δ19.12, 26.60, 26.78, 62.25, 63.07, 68.11, 69.87, 71.76, 73.54, 73.68, 74.60, 74.87, 74.95, 80.76, 101.12, 103.73, 117.85, 127.59, 12.74, 127.87, 129.76, 129.97, 133.83, 135.49, 135.56, 135.83; MS (LSIMS, positive mode) calcd for $C_{47}H_{62}O_{11}Si_2$: 858.4; found: 881.4 (M+Na).

6'6-di-O-tert-Butyldimethylsilyl-3',4'-O-p-methoxybenzyliden e-1-β-o-allyl lactose (11a). A solution of compound 11 (0.23 g, 0.28 mmol), p-methoxybenzaldehyde dimethylacetal (0.143 ml, 0.84 mmol) and a catalytic amount of p-toluenesulfonic acid in 1 ml of anhydrous DMF was heated at 55° C. over 4Å molecular sieves. After 7 h, the solution was neutralized with diisopropylethylamine, diluted with ether, and washed with water and brine. After drying over MgSO$_4$, the product was purified by silica gel chromatography eluting with 2:1 hexanes/ethyl acetate to give 0.12 g (44%) of a 5:1 mixture of diastereomers (determined by $^1H$ NMR analysis). The mixture was carried on to the next step without further purification.

6',6-di-O-tert-Butyldimethylsilyl-3',4'-O-p-methoxybenzyliden e-2',2,3-tri-O-benzovl-1-β-O-allyl lactose (12). To a solution of compound 11a(0.12 g, 0.12 mmol) in 2 ml of anhydrous methylene chloride were added diisopropylethylamine (127 ml, 0.73 mmol) and pyridine (116 ml, 1.44 mmol). The solution was cooled to 0° C. under an argon atmosphere, and benzoyl chloride (85 ml, 0.73 mmol) was added dropwise over a 10 min period. The solution was warmed to room temperature overnight, diluted with ether, washed with water, 0.1M HCl, saturated NaHCO$_3$, and brine, and dried over MgSO$_4$. Purification by silica gel chromatography eluting with 5:1 hexanes/ethyl acetate afforded 154 mg (100%) of a white solid. The mixture of diastereomeric tribenzoates was characterized by $^1H$ NMR and carried on to the next step without further separation.

2',2,3-Tri-O-benzoyl-1-β-O-allyl lactose (13). A solution of anhydrous HCl in methanol was generated by the addition of 0.4 ml of acetyl chloride to 10 ml of anhydrous methanol. This solution (2 ml) was added to a solution of compound 12 (154 mg, 0.119 mmol) in 2 ml of anhydrous ether, and the solution was stirred for 72 h at room temperature. The solution was neutralized with solid NaHCO$_3$, diluted with ether, washed with water and brine, and dried over MgSO$_4$. Purification by silica gel chromatography eluting with 40:1chloroform/methanol afforded 40 mg (48%) of a white solid; $^1H$ NMR (CDCl$_3$) δ2.03 (br s, 2 H), 2.27 (br s, 2 H), 3.08–3.14 (m, 1 H), 3.20–3.25 (m, 1 H), 3.33–3.54 (m, 3 H), 3.69–3.87 (m, 3 H), 4.04 (dd, 1 H, J=13.2, 6.1), 4.17 (app t, 1H, J=9.3), 4.26 (dd, 1 H, J=13.2, 4.7), 4.67–4.71 (m, 2 H), 5.08 (app d, 1 H, J=10.4), 5.16 (app d, 1 H, J=17.3), 5.26 (app t, 1 H, J=8.7), 5.38 (app t, 1 H, J=9.4), 5.60 (app t, 1 H, J=9.4), 5.71 (m, 1 H), 7.33–7.60 (m, 9 H), 7.90 (d, 2 H, J=7.7), 7.98 (d, 2 H, J=7.7), 8.08 (d, 2 H, J=7.7); $^{13}C$ NMR δ60.36, 61.77, 69.57, 70.17, 71.73, 72.75, 73.67, 73.77, 74.22, 75.06, 75.34, 76.91, 99.61, 101.07, 117.71, 128.32, 128.48, 128.58, 128.71, 129.26, 129.49, 129.57, 129.73, 129.86, 133.17, 133.27, 133.38, 165.79, 166.27; MS (LSIMS, positive mode) calcd for $C_{36}H_{38}O_{14}$: 694.2; found: 695.3 (M+H).

6',6-disulfo-1-β-o-allyl lactose (14) and 3',6',6-trisulfo-1-β-O-allyl lactose (15). A solution of 20 mg (0.029 mmol) of compound 13 and 24 mg (0.172 mmol) of sulfur trioxide-trimethylamine complex in 1 ml of anhydrous DMF was stirred at 37° C. over 4Å molecular sieves. The progress of sulfation was monitored as described for compounds 9 and 10. After 20 h, HPLC analysis indicated that compound 12 had been converted into a ca. 1:1 mixture of di- and trisulfates, with a small amount of tetrasulfate beginning to form. The reaction was quenched with methanol and the crude product purified on a column of sephadex LH-20 eluting with DMF. The fractions containing the products were pooled and concentrated, and the residue was dissolved in 6 ml of 5M NH$_4$OH in 50% methanol. The solution was heated at 55° C. for 24 h, the insoluble material was filtered, and the filtrate was concentrated. Chromatography on DEAE-Sepharose eluting with a linear gradient of 2 mM to 2M pyr-OAc (pH 5) afforded separation of the disulfated (eluting at 0.5–0.6M pyr-OAc) and trisulfated (eluting at 1.25–1.6M pyr-OAc) derivatives. The pyridinium salts were converted to sodium salts as described for compound 9 to yield, after lyophilization, 10.4 mg (60%) of compound 14 and 5.6 mg (28%) of compound 15. Only one isomer was observed for each product by $^1H$ NMR analysis; Compound 14: $^1H$ NMR (D$_2$O) δ3.39 (app t, 1 H, J=8.4), 3.56 (app t, 1H, J=9.8), 3.64–3.74 (m, 3 H), 3.83 (m, 1 H), 4.00 (m, 2 H), 4.22–4.33 (m, 4 H), 4.38–4.44 (m, 2 H), 4.54 (d, 1 H, J=8.0), 4.57 (d, 1 H, J=8.1), 5.30 (app d, 1 H, J=10.4), 5.40 (app d, 1 H, J=17.1), 6.01 (m, 1 H); MS (LSIMS, negative mode) calcd for $C_{15}H_{26}O_{17}S_2$: 542; found 563 (M-2 H+Na). Compound 15: $^1H$ NMR (D$_2$O) δ3.40 (app t, 1 H, J=8.4), 3.66–3.76 (m, 3 H), 3.86 (m, 1 H), 4.07 (app t, 1 H, J=6.1), 4.24–4.32 (m, 4 H), 4.38–4.48 (m, 4 H), 4.58 (d, 1 H, J=8.0), 4.65 (d, 1 H, J=7.8), 5.31 (app d, 1 H, J=10.4), 5.41 (app d, 1 H, J=17.2), 6.01 (m, 1 H); MS (LSIMS, negative mode) calcd for $C_5H_{26}O_{20}S_3$: 622.5; found: 643 (M-2H+Na).

Example 3

Synthesis of Lactose 3'-Sulfate

3'-sulfo-1-β-O-allyl lactose (16). A solution of compound 5 (50 mg, 0.13 mmol) and dibutyltin oxide (36 mg, 0.14 mmol) in 2 ml of anhydrous methanol was heated at reflux with 3 Å molecular sieves for.8 h. The solution was filtered through Celite and the filtrate concentrated. The residue was suspended in 2.5 ml of anhydrous acetonitrile and sulfur trioxide-trimethylamine complex (18 mg, 0.13 mmol) was added. The solution was stirred at room temperature under an argon atmosphere for 72 h. The solution was diluted with water (10 ml), filtered through celite and concentrated. Purification on DEAE-Sepharose eluting with a linear gradient of 2 mM to 1M pyr-OAc (pH 5) gave the monosulfate, which eluted at 100–150 mM pyr-OAc. Conversion to the sodium salt followed by lyophilization afforded 37 mg (59%) of the desired product (one isomer by $^1H$ NMR analysis); $^1H$ NMR (D$_2$O) δ3.37 (app t, 1 H, J=8.4), 3.64–3.88 (m, 8 H), 4.02 (m, 1 H), 4.27 (dd, 1 H, J=12.5, 6.2), 4.32–4.46 (m, 3 H), 4.57 (d, 1 H, J=8.1), 4.60 (d, 1 H, J=7.9), 5.32 (app d, 1 H, J=10.3), 5.41 (app d, 1 H, J=16.9), 6.01 (m, 1 H); $^{13}C$ NMR δ58.03, 58.82, 64.77,67.01, 68.57, 70.74, 72.33, 72.64, 72.82, 76.35, 77.95, 99.00, 100.47, 116.63, 131.27; MS (LSIMS, negative mode) calcd for $C_{15}H26O_{14}S$ (462); found: 483 (M-2 H+Na).

Example 4

L-Selectin-GlyCAM-1 Inhibition ELISA

Preparation of GlyCAM-1 for inhibition binding assay. Mouse serum (100 ml, Pel-Freez) was extracted with an equal volume of 2:1 chloroform/methanol, and the layers were separated by centrifugation at 2000×g. The aqueous layer (top) was separated from the organic and precipitated protein layers, concentrated to 50 ml by boiling, and dialyzed against 2×1 L of Dulbecco's PBS at 4° C. This preparation was then diluted to 100 ml with PBS and used as a source of semi-pure GlyCAM-1.

A 96-well microtiter plate (Immulon 2, Dynatech) was coated overnight at 4° C. with a polyclonal antibody specific for the peptide core of GlyCAM-1 (CAM02, 100 ml/well, 1.6–1.9 mg/ml in PBS/0.1% NaN$_3$). The plate was washed with PBS/0.1% tween 20 and blocked with a 3% solution of BSA in PBS (200 ml/well) for 2 h at room temperature. GlyCAM-1 was captured on the wells by incubation with 100 ml/well of the crude GlyCAM-1 preparation described above for 1 h at room temperature. The plate was then washed with PBS/tween in preparation for incubation with L-selectin-IgG and soluble inhibitors.

L-selectin-IgG (4 mg/ml) was preincubated with biotinylated goat anti-human Fc (F(ab')$_2$, Caltag, 2/1000 dilution) and streptavidin-alkaline phosphatase conjugate (Caltag, 2/1000 dilution) in PBS with 0.2% BSA for 25 min at room temperature. Normal rabbit serum (5% v/v) was added and the solution was incubated for an additional 5 min. This solution (70 ml) was combined with 70 ml of a solution of soluble inhibitor in PBS, and then incubated for 30 min at 4° C. The mixture (100 ml) was transferred to the GlyCAM-1-coated wells and incubated for 30 min at room temperature. Finally, the plate was washed quickly with PBS/tween, and the presence of bound L-selectin-IgG was detected by the addition of phosphatase substrate (p-nitrophenyl phosphate, 5 mg/ml in diethanolamine/MgCl$_2$, 100 ml/well) followed by optical density determination at 405 nm (OD 405).

What is claimed is:

1. A method of synthesizing lactose 3'-sulfate, comprising:

(a) reacting gal 1,4βglcβ1-O R$_8$ with dibutyltin oxide to form a stannylene acetal group at the 3'- and 4'-hydroxyl groups of gal β1,4glcβ1-O R$_8$, wherein R$_8$ is an alkyl group, an acetyl group, an acetic acid derivative group, or a linking group;

(b) sulfation with sulfur trioxide, wherein said lactose 3'-sulfate is generated.

2. The method of claim 1, wherein said sulfur trioxide is sulfur trioxide-trimethylamine or sulfur trioxide-pyridine.

3. A method of synthesizing lactose 6'-sulfate, comprising:

(a) stannylene-mediated silylation of gal1,4βglcβ1-O R$_8$ with tert-butyldiphenlsilyl chloride (TBDPSCl), wherein R$_8$ is an alkyl group, an acetyl group, an acetic acid derivative group, or a linking group;

(b) protection of 3'- and 4'-hydroxyl groups by p-methoxybenzylidene acetal;

(c) protection of 2',2, 3, and 6-hydroxyl groups with benzoyl chloride;

(d) methanolysis of the tert-butyldimethylsilyl and p-methoxybenzylidene acetal with HCl in methanol;

(e) sulfation with SO$_3$-trimethylamine at room temperature to produce a reaction mixture comprising benzoate esters; and (f) removal of the benzoate esters with ammonium hydroxide, wherein said lactose 6'-sulfate is produced.

4. A method of synthesizing lactose 3',6'-disulfate, comprising:

(a) stannylene-mediated silylation of galβ1,4glcβ1-OR$_8$, with tert-butyldiphenlsilyl chloride (TBDPSCl); wherein R$_8$ is an alkyl group, an acetyl group, an acetic acid derivative group, or a linking group;

(b) protection of 3'- and 4'-hydroxyl groups by p-methoxybenzylidene acetal;

(c) protection of 2', 2, 3, and 6-hydroxyl groups with benzoyl chloride;

(d) methanolysis of the tert-butyldimethylsilyl and p-methoxybenzylidene acetal with HCl in methanol;

(e) sulfation with SO$_3$-trimethylamine at 37° C. to produce a reaction mixture comprising benzoate esters; and (f) removal of the benzoate esters with ammonium hydroxide, wherein said lactose 3',6',-disulfate is produced.

5. A method of synthesizing lactose 6',6-disulfate, comprising:

(a) protection of 6'- and 6-hydroxyl groups of galβ1,4glcβ1-OR$_8$ with TBDPSCl, wherein R$_8$ is an alkyl group, an acetyl group, an acetic acid derivative group, or a linking group;

(b) protection of 3'- and 4'-hydroxyl groups by p-methoxybenzylidene acetal;

(c) benzoylation of 2', 3, and 2-hydroxyl groups;

(d) methanolysis of the tert-butyldimethylsilyl and p-methoxybenzylidene acetal with HCl in methanol;

(e) sulfation with SO$_3$-trimethylamine at room temperature to produce a reaction mixture comprising benzoate esters; and (f) removal of the benzoate esters with ammonium hydroxide, wherein said lactose 6',6-sulfate is produced.

6. A method of synthesizing lactose 3',6',6-trisulfate, comprising:

(a) protection of 6'- and 6-hydroxyl groups of galβ1,4glcβ1-OR$_8$ with TBDPSCl, wherein R$_8$ is an alkyl group, an acetyl group, an acetic acid derivative group, or a linking group;

(b) protection of the 3'- and 4'-hydroxyl groups by p-methoxybenzylidene acetal;

(c) benzoylation of 2', 3, and 2-hydroxyl groups;

(d) methanolysis of the tert-butyldimethylsilyl and p-methoxybenzulidene acetal with HCl in methanol;

(e) sulfation with SO$_3$-trimethylamine at 37° C. to producea reaction mixture comprising benzoate esters; and (f) removal of the benzoate esters with ammonium hydroxide, wherein said lactose 3',6',6-sulfate is produced.

* * * * *